US00PP15173P2

(12) United States Plant Patent
Trees

(10) Patent No.: US PP15,173 P2
(45) Date of Patent: Sep. 21, 2004

(54) GERANIUM PLANT NAMED 'BALSHOBRILI'

(50) Latin Name: *Pelargonium×hortorum*
Varietal Denomination: Balshobrili

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 10/741,775

(22) Filed: Dec. 19, 2003

(51) Int. Cl.[7] ..... A01H 5/00
(52) U.S. Cl. ..... Plt./329
(58) Field of Search ..... Plt./329

*Primary Examiner*—Kent Bell
(74) *Attorney, Agent, or Firm*—Wood, Phillips, Katz, Clark & Mortimer

(57) ABSTRACT

A new and distinct cultivar of geranium plant named 'Balshobrili' characterized by its bright lilac-colored flowers, dark green-colored foliage, and vigorous upright and mounded growth habit.

1 Drawing Sheet

Latin name of genus and species of plant claimed: *Pelargonium×hortorum.*
Variety denomination: 'Balshobrili'.

BACKGROUND OF THE INVENTION

The present invention relates to a new and distinct cultivar of geranium plant botanically known as *Pelargonium×hortorum* and hereinafter referred to by the cultivar name 'Balshobrili'.

The new cultivar originated in a controlled breeding program in Arroyo Grande, Calif., during May 2000. The purpose of the breeding program was the creation of geranium plants with vigorous upright mounded growth habits, dark green foliage and unique flower colors.

The female parent of 'Balshobrili' was the proprietary *Pelargonium×hortorum* selection designated 'BFP-2807-6' (not patented) characterized by its single, dark lavender-colored flowers, dark green-colored foliage and compact habit. The male parent of 'Balshobrili' was the proprietary *Pelargonium×hortorum* selection designated 'BFP-867-23' (not patented) characterized by its semi-double dark purple-colored flowers, dark green-colored foliage and compact habit. The new geranium was discovered and selected by the inventor as a single flowering plant within the progeny of the above stated cross-pollination during August 2001 at Arroyo Grande, Calif. and was initially designed '2802-6'.

Asexual reproduction of the new cultivar by terminal stem cuttings taken since 2001 at Arroyo Grande, Calif. and West Chicago, Ill., has demonstrated that the new cultivar reproduces true to type, with all characteristics, as herein described, firmly fixed and retained through successive generations of such asexual propagation.

SUMMARY OF THE INVENTION

The new cultivar has not been observed under all possible environmental conditions to date. Accordingly, it is possible that the phenotype may vary somewhat with variations in the environment, such as temperature, light intensity, and day length, without, however, any variance in genotype.

It was repeatedly found that the cultivar of the present invention:

1. Forms semi-double bright lilac-colored flowers,
2. Forms dark green-colored leaves, and
3. Exhibits a vigorous upright and mounded growth habit.

Plants of the new cultivar differ from plants of the female parent primarily in flower form and growth habit and from plants of the male parent primarily in flower color and growth habit.

Of the many commercially available geranium cultivars known to the inventor, the most similar in comparison to 'Balshobrili' is 'SIL ONNO' (disclosed in U.S. Plant Pat. No. 14,647). However, in side-by-side comparisons, plants of 'Balshobrili' differ from plants of 'SIL ONNO' in the following characteristics:

1. Plants of 'Balshobrili' exhibit different flower color than plants of 'SIL ONNO', and
2. Plants of 'Balshobrili' have a more distinct leaf zonation than plants of 'SIL ONNO'.

BRIEF DESCRIPTION OF THE PHOTOGRAPHS

The accompanying photographs show as nearly true as it is reasonably possible to make the same in color illustrations of this type, typical flower and foliage characteristics of the new cultivar. Colors in the photographs differ slightly from color values cited in the detailed description, which accurately describes the colors of 'Balshobrili'. The plants were grown for 8 weeks in a greenhouse at West Chicago, Ill.

DETAILED BOTANICAL DESCRIPTION

Figure 1:
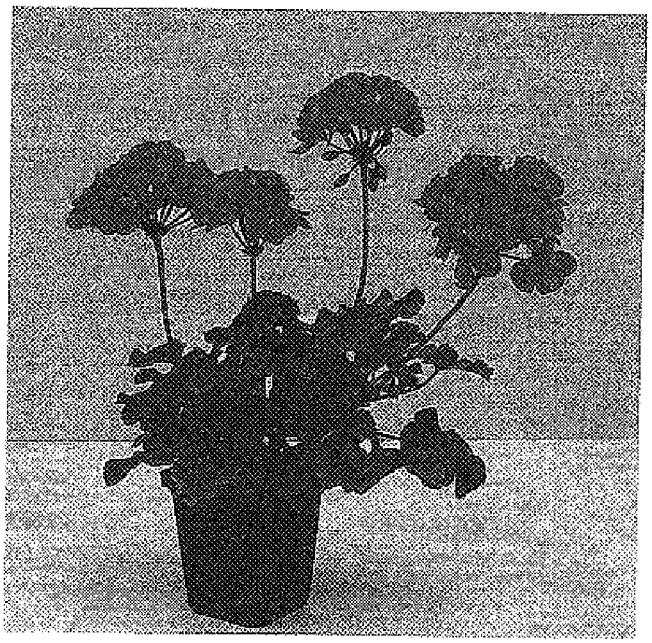
FIG. 1 illustrates a side view of the overall growth and flowering habit of 'Balshobrili'.
Figure 2:
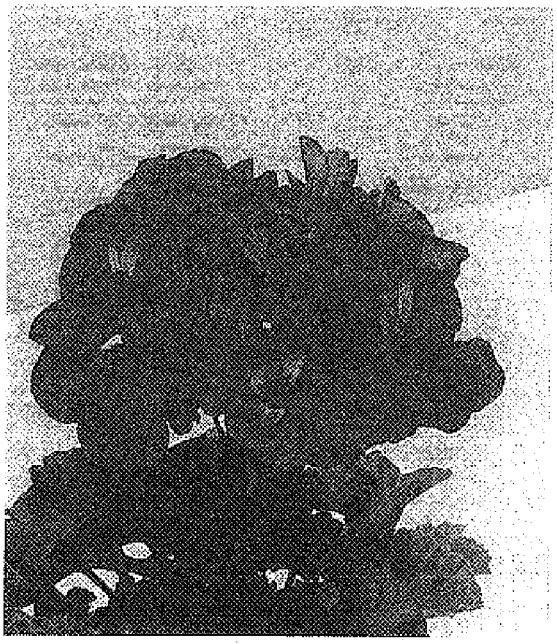
FIG. 2 illustrates a close-up view of a single umbel of 'Balshobrili'.
Figure 3:
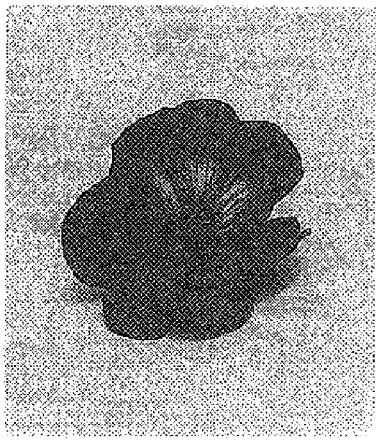
FIG. 3 illustrates a close-up view of a single flower of 'Balshobrili'.

The chart used in the identification of colors described herein is The R.H.S. Colour Chart of The Royal Horticultural Society, London, England, 1995 edition, except where general color terms of ordinary significance are used. The color values were determined on Jul. 30, 2003 in West Chicago, Ill. The readings were taken between 10:00 and 11:45 a.m. under natural light conditions.

The plants used for the following measurements and descriptions were produced from cuttings taken from stock plants and grown in a double polycarbonate covered greenhouse under conditions comparable to those used in commercial practice. The plants were grown in 10 cm pots for 8 weeks utilizing a soilless growth medium in a greenhouse at West Chicago, Ill. Greenhouse temperatures were maintained at approximately 65°–70° F. (18°–21° C.) during the day and approximately 60°–65° F. (15°–18° C.) during the night. Greenhouse light levels of 4,000 to 6,000 footcandles were maintained during the day. Plants were pinched at three weeks after planting.

Botanical classification: *Pelargonium×hortorum* cultivar Balshobrili.

Parentage:

*Female parent.*—Proprietary *Pelargonium×hortorum* selection designated 'BFP-2807-6' (not patented).

*Male parent.*—Proprietary *Pelargonium×hortorum* selection designated 'BFP-867-23' (not patented).

Propagation:

*Type cutting.*—Terminal stem.

*Time to initiate roots.*—Approximately 10 to 14 days.

*Time to develop roots.*—Approximately 21 to 28 days.

*Root description.*—Fibrous.

*Rooting habit.*—Well branched.

Plant description:

*Growth habit and general appearance.*—Vigorous, upright mounded.

*Height.*—From soil level to top of foliage: Approximately 14 cm. From soil level to top of plant plane: Approximately 24.4 cm.

*Width/area of spread.*—Approximately 23.7 cm.

*Branching habit.*—Freely basal branching. Approximately 3 branches per plant. Pinching 14 to 21 days after transplanting helps to improve basal branching.

*Branch description.*—Length: Approximately 7 cm. Diameter: Approximately 9 mm. Color: 144A. Texture: Hirsute. Internode length at center of branch: Approximately 1.3 cm.

*Foliage description.*—Form: Simple. Arrangement: Opposite. Number of leaves per lateral branch: Approximately 11. Shape: Reniform. Margin: Crenate. Apex: Rounded. Base: Cordate. Venation pattern: Palmate. Upper surface texture: Moderately pubescent. Lower surface texture: Moderately pubescent with dense pubescence along veins. Color of mature foliage: Upper surface: 137A with veins of 145A and zone of 147A. Lower surface: 137C with veins of 146A. Size: Mature leaf length: Approximately 4.6 cm. Mature leaf width: Approximately 8.1 cm. Petiole length: Approximately 5.3 mm. Petiole diameter: Approximately 3 mm. Petiole Texture: Pubescent on both upper and lower surface. Petiole color: 144A.

Flowering description:

*Outdoor flowering habit.*—'Balshobrili' is freely flowering under outdoor growing conditions with substantially continuous blooming from spring through fall.

*Time of first flower.*—Approximately 8 weeks after planting of rooted cutting.

*Lastingness of individual bloom.*—Approximately 5–7 days.

Inflorescence description:

*Type.*—Hemispherical umbel. Position: Above foliage. Number of open umbels at any one time: Approximately 2. Number of developing umbels at any one time: Approximately 2. Diameter of fully open umbel: Approximately 10.7 cm. Height (Depth) of fully open umbel: Approximately 6.4 cm. Number of flowers per umbel: Approximately 15.

*Peduncle.*—Strong, erect. Length: Approximately 15.4 cm. Diameter: Approximately 4 mm. Texture: Puberulent. Color: 144A at base with rest of length overlaid with 178A.

Flower description:

*Bud just before opening.*—Shape: Elliptic. Length: Approximately 1.3 cm. Diameter: Approximately 7 mm. Petal color: 67A. Sepal color: 144A with overlay of 187A.

*Corolla.*—Form: Semi-double. Shape: Round, slightly cupped. Diameter/Width: Approximately 4.8 cm. Depth: Approximately 1.8 cm. Fragrance: None. Persistent.

*Petals/petaloids.*—Quantity: Approximately 8 petals and 3 petaloids per flower. Arrangement: Imbricate. Shape: Obovate. Apex: Obtuse. Base: Attenuate. Margin: Entire. Texture of upper and lower surface: Smooth. Upper petal length: Approximately 2.4 cm. Upper petal width: Approximately 1.7 cm. Lower petal length: Approximately 2.1 cm. Lower petal width: Approximately 1.6 cm. Color of all petals: Fully opened, upper surface: Closest to N74A but lighter and more red. Upper petals are N155B at base. Fully opened, lower surface: Closest to 67C with veins of 67A. Upper petals are N155B at base with veins of 67A at base.

*Pedicel.*—Strength: Strong. Angle: Erect. Length: Approximately 3.1 cm. Diameter: Approximately 1 mm. Texture: Densely pubescent. Color: 144B with overlay of 187B.

*Sepals.*—Quantity per flower: 5. Shape: Elliptic. Apex: Acuminate. Base: Truncate. Margin: Entire. Length of largest sepal: 1.1 cm. Width of largest sepal: 3 mm. Length of smallest sepal: 1.1 cm. Width of smallest sepal: 2 mm. Texture of all sepals: Upper surface (inside): Smooth. Lower surface (outside): Puberulent. Color of all sepals: Upper and lower surface: 144A with overlay of 187A especially at base.

*Reproductive organs.*—Androecium: Stamen number: 5 per flower. Filament quantity: Approximately 9. Filament color: N155B. Anther quantity: Approximately 9. Anther length: Approximately 2 mm. Anther color: 71A. Pollen amount: Moderate. Pollen color 168A. Gynoecium: Pistil quantity: One per flower. Pistil length: Approximately 9 mm. Stigma shape: 5 pointed star. Stigma length: 2 mm. Stigma color: 60B. Style length: 2 mm. Style color: 60B. Ovary length: 5 mm. Ovary diameter: 1.5 mm. Ovary texture: Sericeous. Ovary color: 143A.

Seed and fruit production: Neither seed nor fruit production has been observed.

Disease and pest resistance: Resistance to pathogens and pests common to geraniums has not been observed.

Hardiness zone: 'Balshobrili' is presumably hardy in zones nine (9) and above.

What is claimed is:

1. A new and distinct cultivar of geranium plant named 'Balshobrili' substantially as herein shown and described, which:

1. Forms semi-double bright lilac-colored flowers,
2. Forms dark green-colored foliage, and
3. Exhibits a vigorous upright and mounded growth habit.

* * * * *